(12) United States Patent
Eckert et al.

(10) Patent No.: US 7,414,724 B2
(45) Date of Patent: Aug. 19, 2008

(54) LIGHT DIFFUSER USED IN A TESTING APPARATUS

(75) Inventors: Gerd Eckert, Hamburg (DE); Lutz Timmann, Fuhlendorf (DE); Markus Lapczyna, Kaltenkirchen (DE); Arne Schafrinski, Bad Oldesloe (DE)

(73) Assignee: Eppendorf AG, Hamburg (DE)

( * ) Notice: Subject to any disclaimer, the term of this patent is extended or adjusted under 35 U.S.C. 154(b) by 105 days.

(21) Appl. No.: 11/561,103

(22) Filed: Nov. 17, 2006

(65) Prior Publication Data

US 2008/0116382 A1    May 22, 2008

(51) Int. Cl.
*G01N 21/27* (2006.01)

(52) U.S. Cl. .............. 356/411; 356/414; 356/419; 435/303.1

(58) Field of Classification Search ............ 356/73, 356/432–440, 418, 419, 411, 414, 244, 246, 356/319; 435/303.1, 285.1
See application file for complete search history.

(56) References Cited

U.S. PATENT DOCUMENTS

| | | | |
|---|---|---|---|
| 3,516,746 A | 6/1970 | Shibata et al. | |
| 3,981,590 A | 9/1976 | Perkins | |
| 4,159,874 A * | 7/1979 | Dearth et al. | 356/73 |
| 4,343,991 A | 8/1982 | Fujiwara et al. | |
| 4,628,026 A | 12/1986 | Gardell et al. | |
| 5,038,258 A | 8/1991 | Koch et al. | |
| 5,113,069 A | 5/1992 | Parker et al. | |
| 5,294,799 A | 3/1994 | Aslund et al. | |
| 5,427,920 A | 6/1995 | Berndt et al. | |
| 5,482,861 A | 1/1996 | Clark et al. | |
| 5,500,188 A | 3/1996 | Hafeman et al. | |
| 5,534,386 A | 7/1996 | Petersen et al. | |
| 5,825,478 A * | 10/1998 | Wilcox et al. | 356/73 |
| 5,942,432 A * | 8/1999 | Smith et al. | 435/303.1 |
| 5,959,738 A * | 9/1999 | Hafeman et al. | 356/440 |
| 5,973,839 A | 10/1999 | Dorsel | |
| 5,994,707 A | 11/1999 | Mendoza et al. | |
| 6,097,025 A * | 8/2000 | Modlin et al. | 250/227.22 |
| 6,259,562 B1 | 7/2001 | Shie et al. | |
| 7,102,131 B2 | 9/2006 | Spolaczyk et al. | |
| 2003/0160957 A1 | 8/2003 | Oldham et al. | |
| 2005/0110998 A1 | 5/2005 | Lin et al. | |
| 2006/0019265 A1* | 1/2006 | Song et al. | 435/6 |

FOREIGN PATENT DOCUMENTS

| | | |
|---|---|---|
| EP | 0479490 | 4/1992 |
| WO | 2004/069071 | 8/2004 |

* cited by examiner

*Primary Examiner*—Hoa Q Pham
(74) *Attorney, Agent, or Firm*—Rankin, Hill & Clark LLP

(57) ABSTRACT

An apparatus for photometrically testing several specimens each irradiated by a light source, the light altered by the specimens being detected by an optical device and analyzed, the apparatus including a light source, a plurality of sample holders configured adjacent to one another on a support, a detector that receives altered light from sample within the sample holders, the detector including a filter for eliminating interfering light, a sensor having a sensor face and a diffusing optical member located between the filter and the sensor, wherein light is diffused and shines on a greater portion of the sensor surface, and with a more homogeneous brightness as compared to when the light is not diffused.

11 Claims, 3 Drawing Sheets

LIGHT DIFFUSER USED IN A TESTING APPARATUS

BACKGROUND OF THE INVENTION

A device for the photometric measurement of samples is generally disclosed within U.S. Pat. No. 7,102,131 to Spolaczyk et al. Samples within individual sample wells are exposed to radiation from a single light source or a series of light sources and the light modified by the samples, for example fluorescence light, is intercepted by an optical device and is guided to a section of at least one sensor for measuring the intensity and evaluation thereof in an evaluation device arranged downstream of the sensor. The light source(s) are controlled individually by a control device, and the evaluation device and the control device are controlled such that the evaluation device can separate the light from each sample from the light of the other samples. The position of the sample upon, for example, a thermocycler that supports the sample determines the exact position where light modified by the samples shines on the sensor. Small shifts in the position of the sample will slightly shift the area on the face of the sensor where the light from the sample shines.

The inventors of the present invention, through testing have determined that the sensor inherently has different sensitivity levels across its face. Additionally, the sensor is subject to the effect of intensity drift over time. Also, the magnitude of intensity drift varies across the face of the sensor. As a result of these three factors, when the position on the sensor where light from the sample shines changes, measurement results can be difficult to reproduce with good precision. Additionally, if the brightness of the light is not consistent across the section of the sensor upon which the light shines, measurement results are difficult to reproduce. Variations in brightness may be caused by the variations in position of the sample material in sample wells.

It is possible to take the different sensitivity of the sensor area into consideration for every location of the specimens by calibration and determining correction factors, and calculating corrected measurement results with the correction factors. This is a time consuming process and also cannot be used for correcting intensity drift.

What is desired is a way to quickly and easily increase the homogeneity of the sensing qualities of the sensor and as a result improve the precision and reproduceability of measurements recorded from tested samples.

BRIEF SUMMARY OF THE INVENTION

An apparatus for photometrically testing several specimens, each irradiated by a light source, and the light altered by the specimens being detected by an optical device, is provided. The apparatus includes plurality of light sources (each associated with a specimen) or only a single light source, a plurality of sample holders or wells configured adjacent to one another on a support (preferably a thermocycler), a detector that receives altered light from sample within the sample holders, a filter for eliminating interfering light, and a sensor having a sensor face. The detector also includes a light diffusing member (light diffuser), wherein light from a sample is diffused and shines on a greater portion of the sensor face surface as compared to when the light is not diffused.

The filter eliminating interfering light (wavelength filter) is situated in front of the sensor. As regards fluorescence measurements, the filter is a long wavelength filter eliminating residual short wavelength portions of the excitation light illustratively arising as scattered light from the light sources. Bandpass filters are also appropriate for these purposes.

A bundle of optic fibers receives light from the samples and subsequently emits the light. The diffusing optical member is placed between the end of the fiber optic bundle, which first receives the light entering the detector, and the sensor. Preferably, the diffusing optical member is placed directly behind the wavelength filter. The wavelength filter, preferably, is supported in a structure that has the form of a wheel and the diffusing optical member is configured within a circular frame that is screwed to the wavelength filter support structure.

As a result of the diffusing optical member, a sample light beam is placed on a larger percentage of the area of the sensor face and more homogeneous illumination of the sensor is provided. The effects of intensity drift, non-uniform sensitivity across the face of the sensor, and non-uniform intensity drift across the face of the sensor are significantly reduced.

DETAILED DESCRIPTION OF THE INVENTION

The specification of U.S. Pat. No. 7,102,131 to Spolaczyk et al., which issued on Sep. 5, 2006, is hereby incorporated in its entirety by reference.

Figure 1:
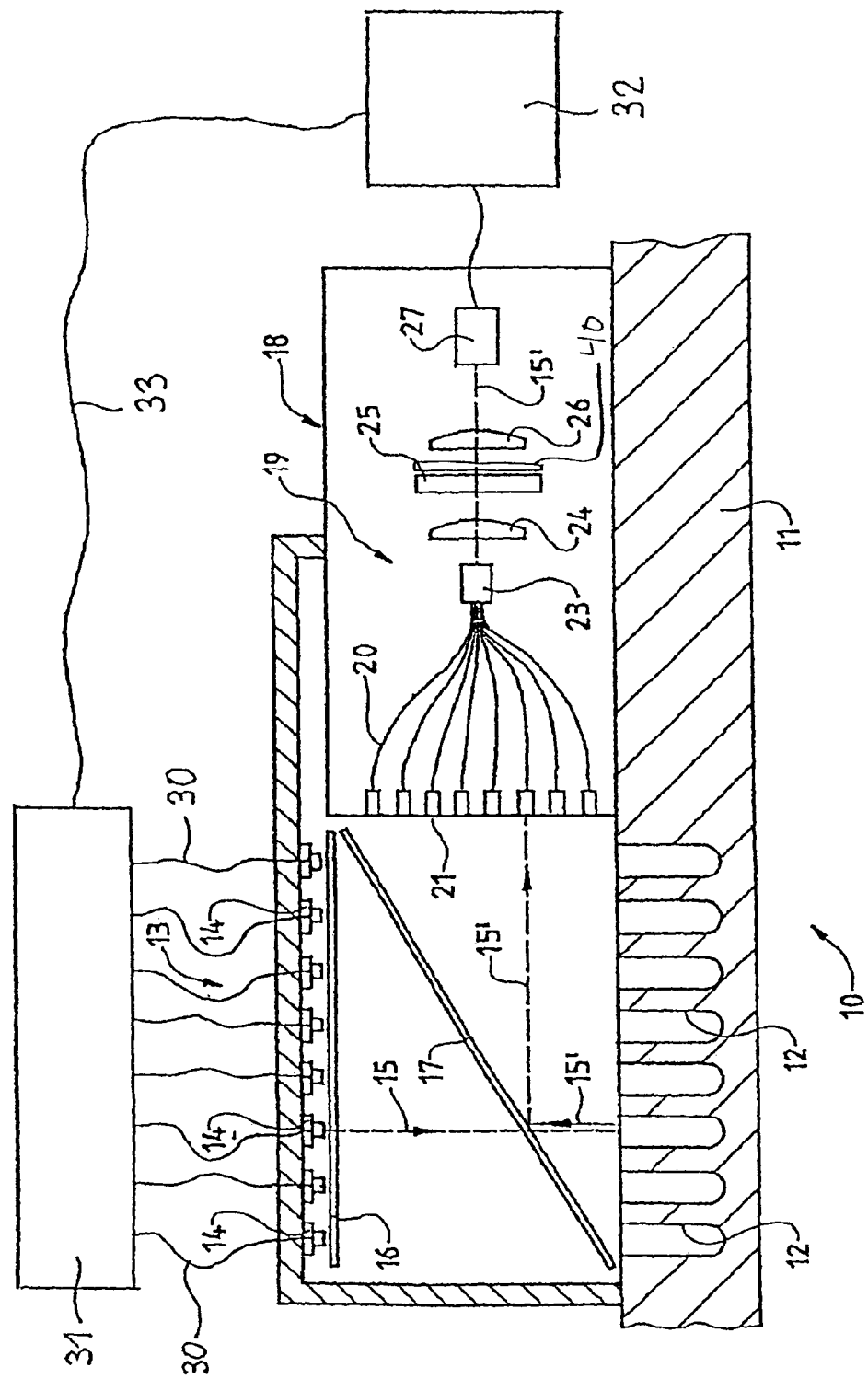
FIG. 1 shows a schematic view of a device for photometric measurement of several samples including a diffusing optical member.

Referring to FIG. 1, the apparatus 10 comprises a schematic, conventional thermocycler 11 with wells 12. Reaction vials (not shown) are in place in the wells 12. Each vial contains one sample with one or more fluorescence indicators.

A covered housing 13 fitted with an illumination unit of several LEDs 14 is set on the thermocycler 11. One LED 14 is allocated to each well 12. Preferably, the LEDs 14 are configured as an array. Each LED 14 points in a direction such that it will irradiate only one associated well 12 and, if possible at all, not the adjacent wells. The LEDs 14 may, in particular, be laser diodes. The LEDs 14 are connected by cables 30 to a control unit 31 which is in turn connected by a cable 33 to an analyzer 32. Alternatively, a single source of light may be used.

An illustrative light path is denoted by 15, 15'. The light 15 is radiated from the LED 14 and first passes through an optional, but preferred, short wavelength filter 16 by means of which long wavelength components are filtered out. Then the light 15 passes through a beam splitter 17, which, in this instance, preferably shall be wholly transmitting.

The light 15 radiated from the LED 14 will excite a fluorescence indicator contained in a sample in the well 12. The indicator, in turn, emits a fluorescence signal 15'. The beam splitter 17 is designed such that the fluorescence signal 15' is reflected laterally. A dichroic mirror is preferably used as the beam splitter 17 and will transmit the excitation light while reflecting the emitted, longer wavelength fluorescence signal.

The reflected fluorescence signal 15' is then sensed by a detector 18. The detector 18 is fitted with an optical device 19 that can reproduce the fluorescence signal 15' onto a light sensitive sensor 27.

In lieu of the typical large-area lens element, the collimator in the optical device 19 is an array of optic fibers 20. The optical fiber array catches the light from the wells 12 reflected by the beam splitter 17 by means of the mutually spaced light input areas 21 and harnessing optic fibers 20 so as to transmit the light through parallel harness ends at 23.

Contrary to a collimator composed of lens elements, the collimator configuration of a bundle of optic fibers 20 offers the feature that the light exiting the bundle optic fibers at 23 is collimated more narrowly. That feature is especially advantageous when, for instance, interference filters offering a spectral transfer function that depends on the light's angle of incidence are configured subsequently.

Next, the fluorescence signal 15' is reproduced through the optic fibers harness 23, through a lens element 24, through a long wavelength filter 25, and a further lens element 26 onto a sensor 27, preferably a channel photo multiplier. The long wave pass filter 25 is required in order to filter any shorter wavelength regions out of the excitation light.

Figure 4:
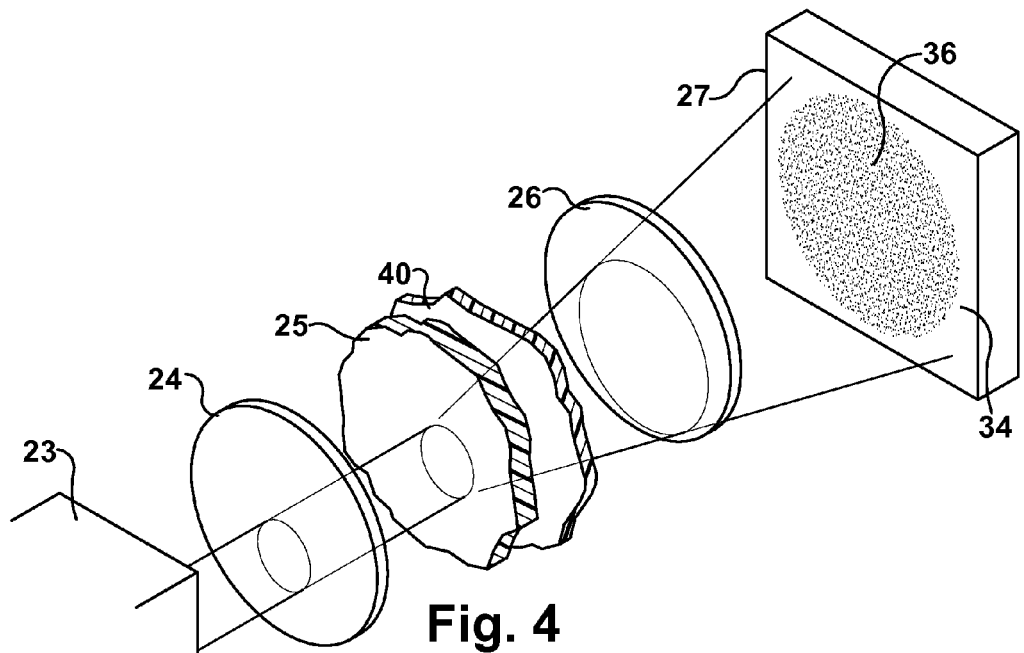
FIG. 4 is a perspective view of light passing through optical elements of the device while utilizing the diffusing optical member.

Referring to FIGS. 1 and 4, additionally, a diffusing optical member 40 is placed between the end of the fiber optical bundle 23 and the sensor 27. The diffusing optical member 40 is for example a "light shaping diffuser" sold by Physical Optics Corporation of Torrance, Calif. The diffusing optical member 40 is preferably in the form of a thin panel, having a thickness of approximately 0.5 millimeters or less. The diffusing optical member 40 transmits at least 70% of the altered light applied thereto and preferably at least 90% of the altered light. The diffusing optical member 40 has a predetermined angular distribution so as to illuminate a large predefined area 36 of the sensor face 34. The exact position of the focus area 36 on the sensor face 34 depends on the location of the specimen on the thermocycler 11 or the sample within a sample well. Different locations cause slight variations in the position of the focus area 36.

Figure 5:
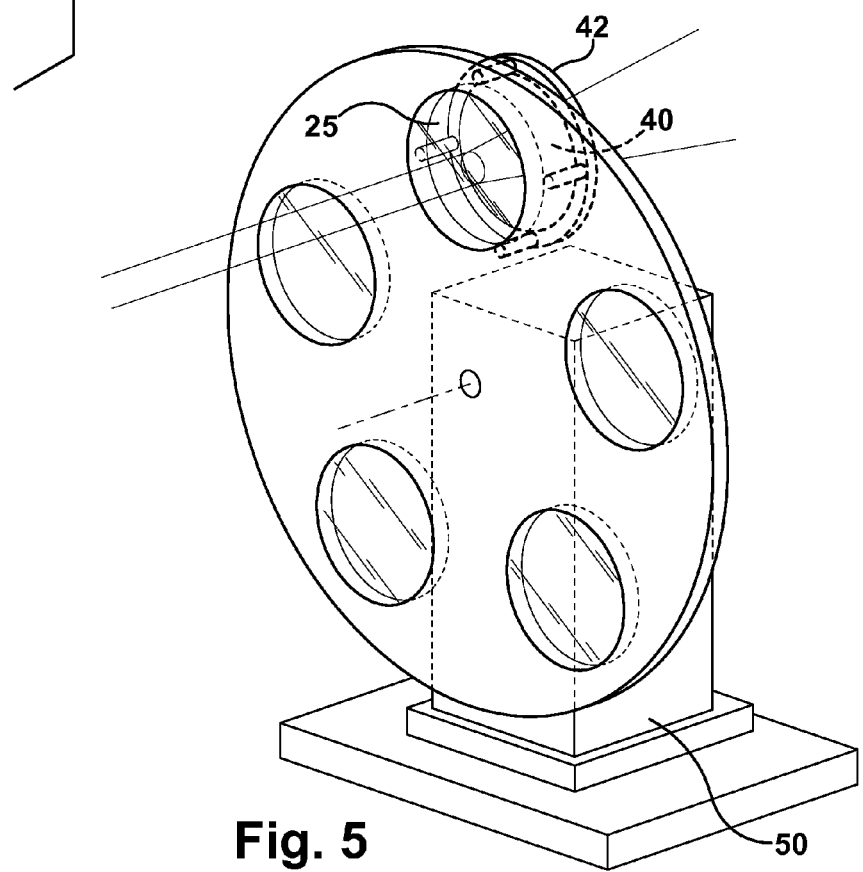
FIG. 5 is a perspective view of a wavelength filter wheel support structure including the diffusing optical member.

Preferably, the diffusing optical member 40 is arranged directly behind the long wavelength filter 25, although the diffusing optical member 40 may be located anywhere between the optic fiber bundle 23 and the sensor 27. Referring to FIG. 5, in one embodiment of the invention, the diffusing optical member 40 is secured to a circular frame 42 and the frame 42, in turn, is screwed to the long wavelength filter support structure, directly adjacent to the wavelength filter 25. The long wavelength filter 25, preferably is one of a group of filters supported within the rotatable wheel-like support structure 50. Each different filter 25 in the group has different filtering properties and can easily be placed into the optical path by rotating the wheel like structure 50. Alternatively, a large diffusing optical member may be used that optically covers the whole wheel-like structure 50. The holographic area of the diffusing optical member 40 is placed in the direction of the wavelength filter 25 and as a result effects a reduction of transmission loss due to lowered reflections on the surface of the diffusing optical member 40.

Referring to FIG. 4, the diffusing optical member 40 diffuses a beam of light, so that a larger portion of the sensor (compared to a system without a diffusing optical member) is exposed to the reflected light of the sample.

Because the sensor face predefined focus area 36, exposed to light from the sample, is larger when using the diffusing optical member, the effects of (1) varying sensitivity across the sensor face 34, (2) intensity drift and (3) varying intensity drift across the sensor face 34, are mitigated.

Figure 2:
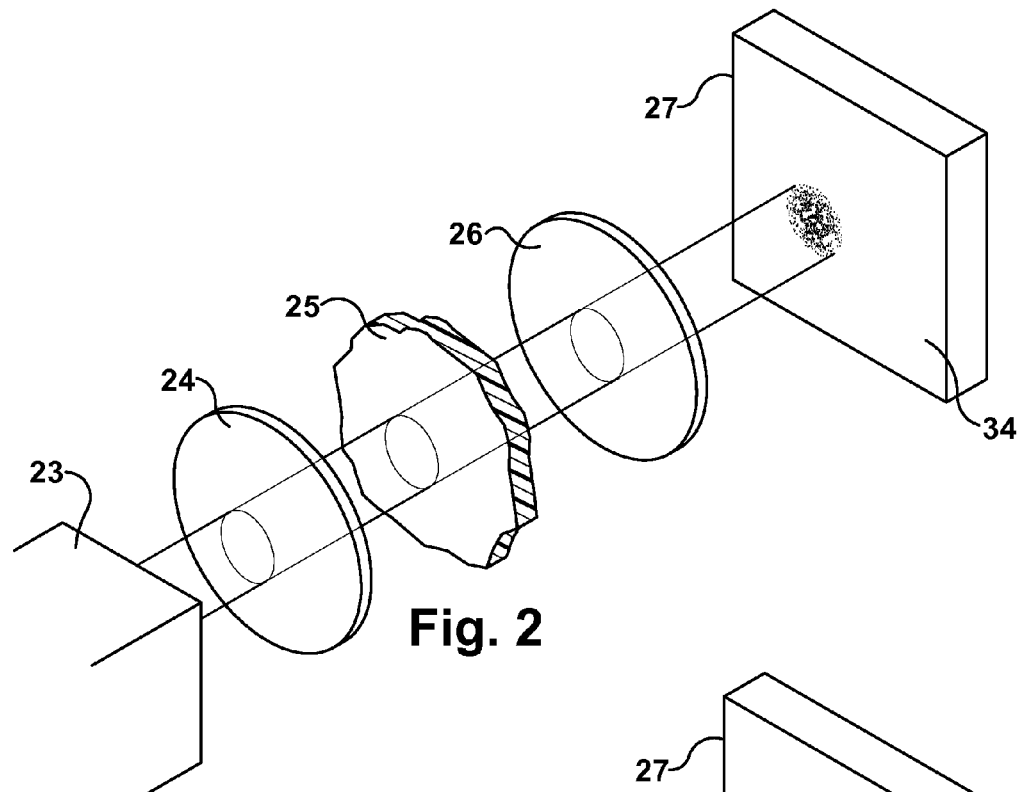
FIG. 2 is a perspective view of light passing through optical elements of the device without utilizing the diffusing optical member.
Figure 3:
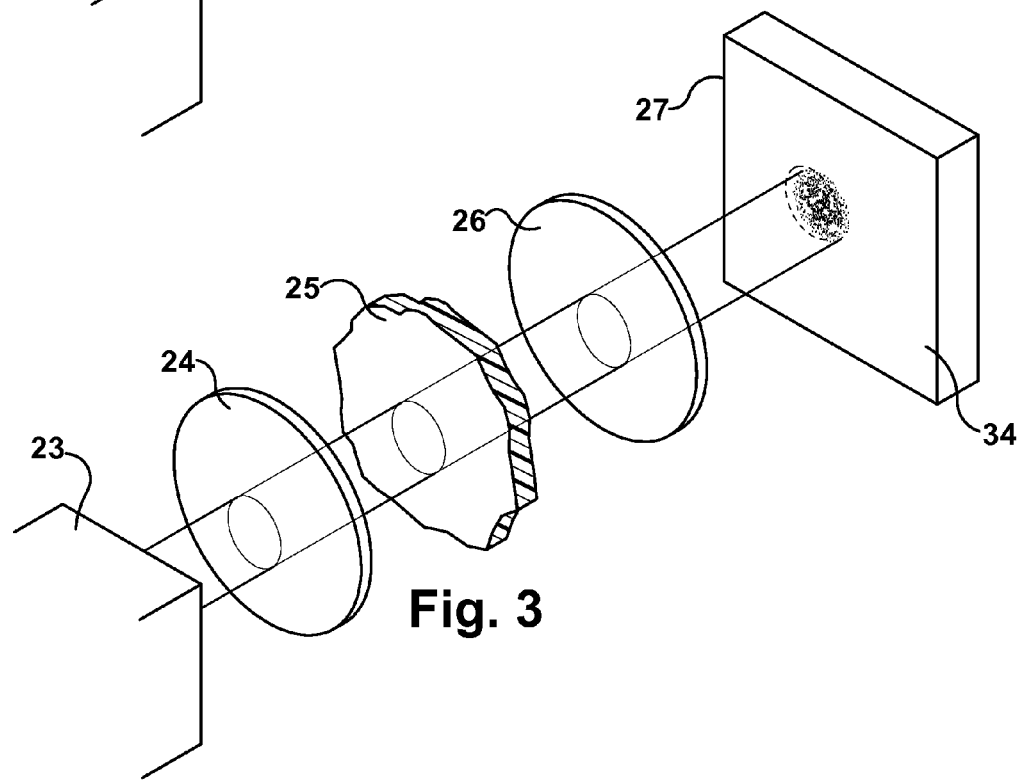
FIG. 3 is a perspective view of light from a different sample well passing through optical elements of the device without utilizing the diffusing optical member.

Additionally, any positional shifts due to different sample locations are mitigated. For example, referring to FIG. 2, light from a first sample is shown on the sensor face 34. Referring to FIG. 3, light from a second sample, placed in the identical well 12 on the thermocycler, but in a different position, or in an adjacent well, may shine on the sensor face 34 in a slightly different position (original position shown in broken lines). Because of the effects of variations in sensitivity, intensity drift, and variations in intensity drift, sensor readings made from these two adjacent positions will likely not be the same when testing identical samples. However, referring to FIG. 4, where the light reflected from the sample is diffused, virtually the same area of the sensor is covered, no matter what variations there are in sample wells or in the position of the sample within the sample well 12. Thus, the effects of sensitivity, intensity drift, and variations in intensity drift, are mitigated.

Additionally, the diffusing optical member 40 creates fewer variations in brightness across the focus area 36 on the sensor which also mitigates the effects of the three factors listed above.

As an alternative embodiment of the invention, the diffusing optical member may also be provided in the form of a film that is applied to the surface of the wavelength filter 25. The diffusing optical member may be mounted in front of the lens element 26 which is a collecting lens.

Although the invention has been shown and described with reference to certain preferred and alternate embodiments, the invention is not limited to these specific embodiments. Minor variations and insubstantial differences in the various combinations of materials and methods of application may occur to those of ordinary skill in the art while remaining within the scope of the invention as claimed and equivalents.

What is claimed is:

1. An apparatus for photometrically testing several specimens each irradiated by a light source, the light altered by the specimens being detected by an optical device and analyzed, the apparatus comprising:
   a light source;
   a plurality of sample holders configured adjacent to one another on a support;
   a detector that receives altered light from sample within the sample holders, the detector comprising:
      a filter for eliminating interfering light from the altered light;
      a sensor having a sensor face; and
      a diffusing optical member, wherein the altered light from a sample within a sample holder is diffused and shines on a greater portion of the sensor face and with more homogeneous brightness across the illuminated sensor face compared to when the light is not diffused.

2. The apparatus of claim 1, wherein the diffusing optical member is located between the filter and the sensor.

3. The apparatus of claim 1, the detector further including a series of optical fibers that in a large array receive altered light from the samples and reduce the received light to a small array that is then directed at the filter for eliminating interfering light.

4. The apparatus of claim 1, wherein the filter eliminating interfering light is one of a group of selectable filters supported within a rotatable wheel-like structure.

5. The apparatus of claim 4, wherein the diffusing optical member is spaced from the filter and supported in a circular frame that is removably attached to the filter.

6. The apparatus of claim 1, further including a focusing lens.

7. The apparatus of claim 6, wherein the diffusing optical member is located between the filter eliminating interfering light and the focusing lens.

8. The apparatus of claim 1, wherein the diffusing optical member is a holographic diffuser.

9. The apparatus of claim 8, wherein the diffusing optical member transmits therethrough at least 70 percent of the altered light received.

10. The apparatus of claim 9, wherein the diffusing optical member transmits therethrough at least 90 percent of the altered light received.

11. An apparatus for photometrically testing several specimens each irradiated by an associated light source, the light altered by the specimens being detected by an optical device and analyzed, the apparatus comprising:

a plurality of light sources;

a plurality of sample holders configured adjacent to one another on a support;

a detector that receives altered light from sample within the sample holders, the detector comprising:

a filter for eliminating interfering light from the altered light;

a sensor having a sensor face; and a diffusing optical member, wherein the altered light from a sample within a sample holder is diffused and shines on a greater portion of the sensor face and with more homogeneous brightness across the illuminated sensor face compared to when the light is not diffused.

* * * * *